(12) United States Patent
McGee et al.

(10) Patent No.: US 6,354,135 B1
(45) Date of Patent: Mar. 12, 2002

(54) OBTENTION AND ANALYSIS OF ODORS FROM ODOR EMITTERS

(75) Inventors: Thomas McGee, Orangeburg, NY (US); Kenneth Leo Purzycki, Lake Parsippany, NJ (US)

(73) Assignee: Givauden Roure (International) SA, Geneva (CH)

( * ) Notice: Subject to any disclaimer, the term of this patent is extended or adjusted under 35 U.S.C. 154(b) by 0 days.

(21) Appl. No.: 09/295,848

(22) Filed: Apr. 21, 1999

Related U.S. Application Data
(60) Provisional application No. 60/083,275, filed on Apr. 28, 1998.

(51) Int. Cl.$^7$ ............... G01N 1/24; G01N 30/00; G01N 33/00
(52) U.S. Cl. ............ 73/23.34; 73/863.21; 73/863.23
(58) Field of Search ............ 73/23.34, 863.21, 73/863.23, 864.51

(56) References Cited

U.S. PATENT DOCUMENTS

| | | | |
|---|---|---|---|
| 4,257,796 A | * 3/1981 | Arkenbout | 62/538 |
| 4,384,957 A | * 5/1983 | Crowder, III et al. | 210/656 |
| 5,310,681 A | 5/1994 | Roundbehler et al. | 436/106 |
| 5,331,843 A | * 7/1994 | Gramatte et al. | 73/54.09 |
| 5,369,978 A | 12/1994 | Mookherjee et al. | |
| 5,795,368 A | * 8/1998 | Wright et al. | 95/82 |
| 6,004,443 A | * 12/1999 | Rhodes et al. | 204/454 |

FOREIGN PATENT DOCUMENTS

| | | |
|---|---|---|
| EP | 0 714 020 | 5/1996 |
| EP | 0 915 329 | 5/1999 |

OTHER PUBLICATIONS

Mookherjee, et al., *Perfume and Flavorist*, vol. 23, pp. 1–11 (1998).
Feray, et al., *Journal of Chromatography A*, vol. 750, pp. 63–74 (1996).
Kaiser, R., *The Scent of Orchids*, F. Hoffmann–La Roche AG, Basle, Switzerland, pp. 17–28 (1993).
Neuner–Jehle et al., "The Measuring of Odors," *Perfumes: Art, Science and Technology*, P.M. Müller and D. Lamparsky, eds. Elsevier Applied Science: London, pp. 153–212 (1991).
Kaiser, R., "Trapping, Investigation and Reconstitution of Flower Scents," *Perfumes: Art, Science and Technology*, P.M. Müller and D. Lamparsky, eds. Elsevier Applied Science: London, pp. 213–250 (1991).
Derwent English language abstract of EP 0 714 020 A2.

* cited by examiner

*Primary Examiner*—Daniel S. Larkin
(74) *Attorney, Agent, or Firm*—Bryan Cave, LLP

(57) ABSTRACT

Aroma chemicals emitted from an aroma-emitting source are obtained by an apparatus and process for obtaining the chemicals. The apparatus includes the use of one or more capillary tubes which have on their interior surfaces an absorbent material, a suction device for drawing the aroma chemicals through the capillary tubes, and a connecting tube which connects the capillary tubes and the suction device. A system for collecting and analyzing the aroma chemicals emitted from an aroma-emitting source is disclosed which has one or more capillary tubes, a suction device, a connecting tube, a thermal desorber which desorbs the aroma chemicals directly from the capillary tubes, a cryogenic focusing device, and a gas chromatograph/mass spectrometry instrument.

21 Claims, 6 Drawing Sheets

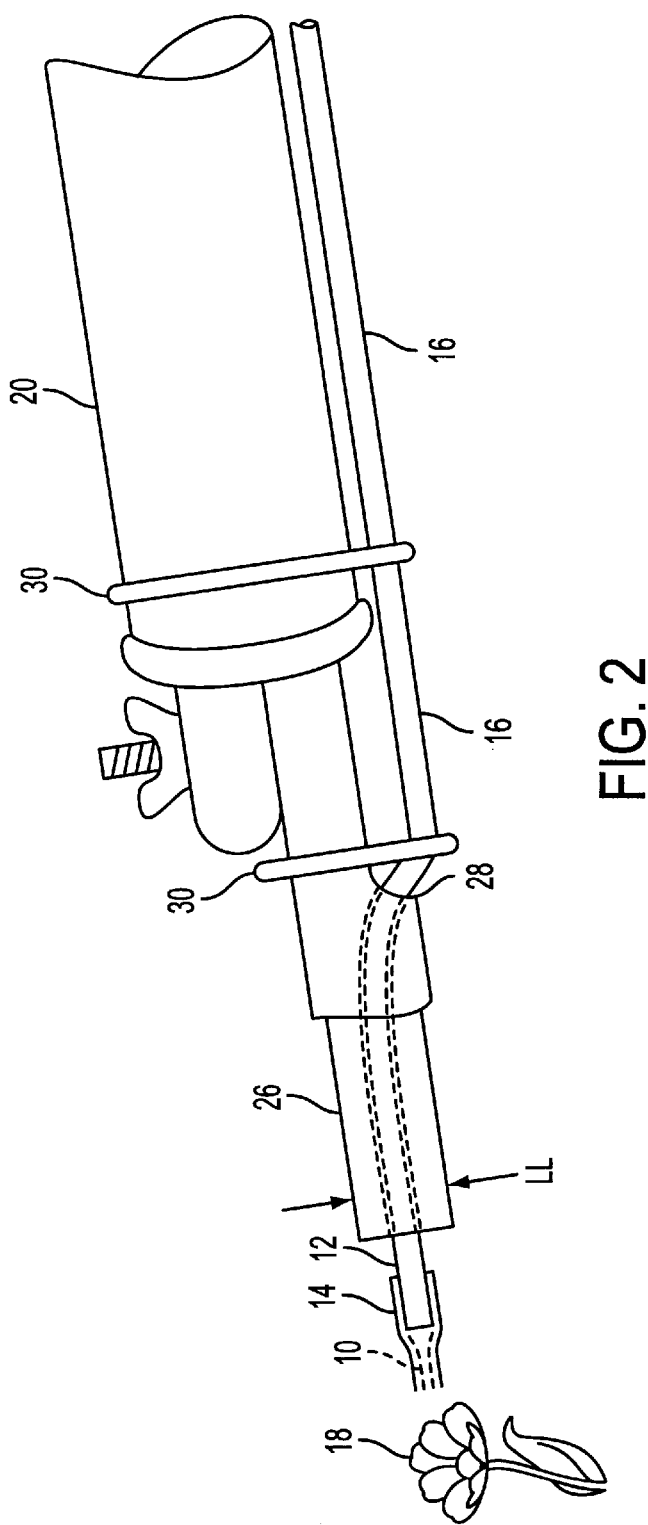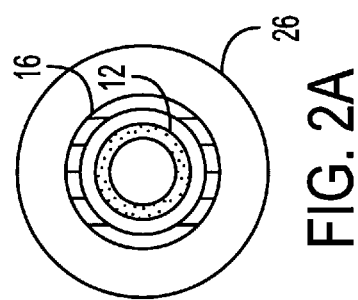

OBTENTION AND ANALYSIS OF ODORS FROM ODOR EMITTERS

This application claims the benefit of U.S. Provisional Application No. 60/083,275 filed Apr. 28, 1998.

FIELD OF THE INVENTION

The present invention relates to obtaining odors from odor emitting objects. More particularly, the present invention relates to an apparatus and process for acquiring odor(s) emitted from odor emitting objects.

BACKGROUND OF THE INVENTION

The emission of odor(s) from objects has given rise to attempts to copy or to acquire odors of interest. For example, aromas from botanical sources, such as living flowers, leaves or other parts of living trees or plants, are sought after in the perfumery arts.

A technique for capturing and analyzing the scent of flowers is described in Perfumes Art Science and Technology edited by P. M. Muller and D. Lamparsky and summarized by R Kaiser in The Scent of Orchids. The method disclosed involves placing a living flower, which is part of a living plant or tree, into an enclosed glass vessel. The glass vessel must be of suitable size and shape to permit the flower to be enclosed without damaging the plant or flower. Specially designed glassware is often required to accommodate particular types of flowers.

When such vessels are employed, the aroma chemicals surrounding a flower. i.e. the headspace, fill the vessel with a vapor phase. The headspace volatiles are drawn through an adsorption trap by means of a pump, over a period of thirty minutes to two hours. Adsorbents commonly employed in the trap are activated charcoal or special polymeric materials, such as TENAX® (2,6-diphenylene polymer) or Porapak Q® (ethylvinylbenzene-divinylbenzene copolymer). The trapped aroma chemicals are eluted from the trap with a solvent, and injected into a gas chromatograph and analyzed by mass spectrometry (GC/MS).

Mookherjee, et al., U.S. Pat. No. 5,369,978, which is incorporated herein by reference, discloses improvements in the above noted method, although essentially the same principles apply.

In addition, a technique using solid phase micro extraction (SPME) has been described by Mookherjee, et al., Perfumer and Flavorist 23, pp. 1–11 (1998). This technique requires placing a single SPME needle, which is a 2–3 mm solid glass fiber coated with a high boiling point liquid adsorbent, in close proximity to a flower for thirty minutes to sixty minutes. The aroma molecules are adsorbed onto the needle-like glass fiber and are then analyzed by GC/MS.

Great difficulty, however, has been encountered in attempting to collect scents from certain aroma sources using conventional aroma collecting devices. Special glassware for enclosure of flowers can be inconvenient to use, particularly when the flowers are not readily accessible. Also, they can be awkward to carry to and from remote locations. The rain forest, for example, has a cornucopia of fragrant scent-emitters. However, flowers are often at the end of high slender branches in the forest canopy and are difficult to reach.

Additionally, it is very difficult to attach the conventional collecting devices to the outer branches of trees. Often they do not support the weight of either a person or the equipment employed to collect a sample, particularly in view the length of time required, which can thwart efforts to obtain aromas from some sources.

With respect to the SPME technique, SPME needles are very delicate. The single needle employed to obtain the scent may break at any time in dense canopy. In fact, more often than not, such needles may break during capture in such an environment. Additionally, the time required to adsorb the aroma chemicals using the SPME needles can exceed thirty minutes, making it impractical for remote collections.

SUMMARY OF THE INVENTION

The present invention addresses these problems by providing an apparatus for obtaining odor(s) emitted from an odor emitting source. The apparatus of the present invention includes an adsorption unit having at least two openings, which may be one or more capillary tubes. The interior surfaces of the tubes comprise an adsorbent material for adsorbing odor chemicals. A suction device for drawing odor chemicals into the adsorption unit, is positioned for and connected to the tube assembly and a connector connects the tube assembly and the drawing device.

The invention also provides a process for obtaining or capturing odor chemicals. The process includes placing an adsorption unit, which comprises on its interior surface an adsorbent material for trapping aroma chemicals, in proximity to an aroma-emitter, and drawing aroma chemicals into an opening of the adsorption unit with a gas drawing means which is operably connected to the adsorption unit.

The invention also provides an apparatus for obtaining odor chemicals, which includes an adsorbing unit containing an interior surface of an adsorbent material, a suction device for drawing the odor chemicals into the unit, and a connecting tube which connects the unit and the suction device.

The invention further provides a system for collecting and analyzing the odor chemicals emitted from an odor-emitting source, which includes a plurality of capillary tubes which contain interior surfaces having at least one adsorbent material for trapping odor chemicals, a suction device for moving the air containing odor chemicals throughout the plurality of capillary tubes, a connecting tube which connects the plurality of capillary tubes and the suction device and provides an air-tight seal there between, a thermal desorber disposed to hold the plurality of capillary tubes, for thermally desorbing odor chemicals trapped within, a cryogenic focusing device, and a gas chromatograph equipped with a mass spectrometry detector.

The invention also provides a process for obtaining odor chemicals from an odor-emitting source, which includes providing a plurality of capillary tubes containing interior surfaces having adsorbent material for adsorbing odor chemicals, placing the plurality of capillary tubes in proximity to an odor-emitter, and drawing the odor chemicals into the capillary tubes with a suction device which is operably connected to the plurality of capillary tubes for from two to fifteen minutes.

The invention further provides an apparatus for obtaining odor chemicals, which includes an adsorption unit having surface areas of an adsorbent material and a suction device for drawing air containing odor chemicals across the surface of the adsorbent material.

Further, the invention allows for the thermal desorption of adsorbed sample cryogenic focusing, and resolution and identification odor components by GC/MS.

It is an object of the present invention to provide an apparatus for obtaining aroma chemicals from, in particular, difficult to reach aroma emitters.

It also is an object of the present invention to provide an apparatus which is readily portable and is durable for obtaining aroma chemicals from, in particular, a dense canopy.

It also is an object of the present invention to provide a process for obtaining aroma chemicals from, in particular, difficult to reach aroma emitters.

It is a further object of the invention to provide a process for obtaining aroma molecules which facilitates a short capture time.

DETAILED DESCRIPTION OF THE INVENTION

The apparatus for obtaining odors includes an adsorption unit, a suction device for drawing the odor chemicals into the adsorption unit, and a connector for connecting the adsorption unit and the suction device.

The adsorption unit has an opening for receiving odor chemicals and an opening displaced away from the first for drawing the odor chemicals through. The adsorption unit can be a tube or preferably, a plurality of tubes. A plurality of capillary tubes are the most preferred type of adsorption unit. As used herein, the term odor includes, but is not limited to aromas, as for example, fragrant scents.

The type and dimensions of the tubes of the adsorption unit may vary. For example, a single tube having a plurality of crossing wall portions contained within the tube are considered to be an equivalent alternative to the plurality of capillary tubes. Similarly, tubes having concentric tubes of decreasing diameter contained within a tube also are considered to be equivalent, because of the favorable surface area exposed to odor chemicals. Generally, the inside diameter of the capillary tube ranges from about 0.07 mm to about 1.0 mm, and more preferably from about 0.75 mm to about 0.9 mm.

The interior surface(s) of the adsorption unit are coated with an adsorbent material for adsorbing odor chemicals from the air to the stationary material. It is also contemplated that the adsorption unit integrally have interior surface(s) of an adsorbing material. As used herein, an adsorption unit which comprises an adsorbent material on its surface(s) encompasses both of these situations.

The adsorbent employed can vary depending on the odor chemicals sought to be obtained. Generally adsorbent materials, e.g., charcoal, may be used. Preferably, highly adsorbent materials of differing polarity are used to ensure that all aroma chemicals are obtained. The adsorbent material can be selected from the group consisting of a polar adsorbent, a non-polar adsorbent, an intermediate polarity adsorbent, and any combination thereof. A portion of the capillary tubes may be internally coated with a polar adsorbent, another portion with a non-polar adsorbent, and another portion with an intermediate polarity or neutral adsorbent. Examples of adsorbent materials that are useful in the practice of the invention are Carbowax 20-M as a polar phase adsorbent, methyl silicone as a non-polar adsorbent, and phenyl methyl silicone and polyacrylate as intermediate polarity adsorbents. These materials are coated on the inside of the capillary tube to a thickness of from about 0.1 $\mu$m to about 1.25 $\mu$m, preferably from about 0.1 to about 0.7 $\mu$m, and most preferably from about 0.15 $\mu$m to about 0.7 $\mu$m In addition, while preferred tubes for obtaining flower aromas are capillary tubes made from fused silica, alternative tubes may be made of different types of materials which may not be required to be coated per se or which may be made, for example, of metal, of glass, of tempered glass, of a polymer, or of a polymer composite.

The length and number of tubes depends upon the scent emitting source. In general, at least one tube is required. Preferably, three tubes of each selected phase are used. The total number of tubes in the bundle is such that the bundle will fit inside a typical thermal desorption tube of a thermal desorption device. For example, the Gertsel Thermal Desorption System TDS 2 instrument requires that the bundle fit into a tube having an internal diameter of about 4 mm. The length of the capillary bundle is from about 5 mm to about 120 mm, usually from about 15 mm to about 120 mm, and more preferably from about 20 mm to about 40 mm.

The capillary bundle is held within the distal end of the connecting tube in an air-tight manner. The connecting tube is of a flexible material such as, for example, PTFE (Teflon), nylon, polypropylene, polyethylene, and the like. The diameter of the connecting tube should be such that the bundle of capillaries fit snugly within an air-tight seal, or another fastening device. Typically, the connection is made of heat-shrink tubing.

The capillary bundle can be suspended in proximity to the aroma emitting source by holding the connecting tube so that the free end of the capillary tubes are held in place, usually over a flower. When the opening of the capillary tubes which is not attached to the connecting tube is placed in proximity with an aroma emitter, the suction device is activated and the aroma chemicals are drawn through the coated capillary tubes from about two to about fifteen minutes. A two to five minute collection time is usually sufficient, particularly for the major components. A five to fifteen minute collection time may be used for components that are present in smaller amounts. The suction device is any device which draws a fluid such as a gas, preferably the headspace air, through each coated capillary tube at a controlled rate. For example, the suction device can be a pump, such as a piston pump, a vane pump, a diaphragm pump, a peristaltic pump, or can be a fan. Consequently, a sufficient amount of odor chemicals are adsorbed onto the adsorbent material in a relatively short amount of time to permit analysis the odor components.

Especially useful are suction devices that do not let the gas being drawn through the capillaries come into direct contact with the suction device itself, thus avoiding contamination. An example of such a suction device is a diaphragm pump that is capable of pumping air from 10–100 ml per minute. The rate can change depending on the composition of the bundle and the number of tubes in the bundle. For example, for a bundle of twenty-four tubes, the optimal flow rate was from about 40 to 60 ml gas per minute. The pump may be operable by conventional means such as by electric current or battery. For trips to remote locations for scent capture, a battery operated pump is used. The pumping rate of the suction device is adjusted using a flow metering device so that the amount of gas passing through the array of capillary tubes in a given time can be measured. Thus, air may be drawn or moved into and through the coated tubes from about two to fifteen minutes or longer, if desired.

Advantageously, the apparatus has a support for supporting or securing the capillary tubes, and additionally, a housing sheath within which the plurality of capillary tubes are disposed such that they are freely moveable with the connector. Also advantageously, the apparatus includes a means for extending the tube assembly beyond the end of the housing sheath for collection of odor chemicals.

Preferably, the connecting tube holding the capillaries is supported or held by a support such as a rigid rod. The support is of fairly rigid material such as glass, metal, wood, or stiff polymeric materials. The support can be any practicable length for reaching odor sources in high branches. Of great use for also reaching aroma sources that are hard to access is a light weight extendible tubular pole which permits the collection device to be extended with the arm portion angled such that the distal end of the device reaches over a flower. The pole can be made of aluminum or the like for a sturdy, light-weight construction. When using an extendible pole, the support can be affixed to the distal end or integral therewith. In addition, the pole can be collapsed for easy transport.

The extendible pole can in practicality be up to eight feet long when fully extended, but can reach upwards of twenty feet in length, especially when additional sections are connected to the pole. It is advantageous for the extendible pole to be foldable for ease of carrying to about a three and one-half feet length. There should be at least one hinging arm portion for extending at a different angle from that of the adjacent portion. If there is only one arm portion, it should be at the distal end for extending the capillaries. How far the pole is extended and at what angle, if any, the arm is extended, depends upon the distance and accessibility of the flower.

Any extension pole used accommodates the connecting tube either alongside or within the pole. To accommodate the connecting tube within the pole, the pole should be hollow, with enough room in the hollow space of the tubing to run through. There must also be sufficient play for the connecting tube at the hinging points when the arm is angled. It is preferable, however, to run the connecting tube alongside the extendible pole, so that the tube need not be flexed as much by the hinging portion of the arm.

Whether the support at the distal end is integral or attached to the pole, the support itself must support or hold the connecting tube which holds the bundle of capillaries. The support is preferably tubular with a sufficient hollow interior area to accommodate the connecting tube. The support can be attached to the pole such that it can swivel, to provide even further flexibility for accessing a particular flower in dense foliage.

The capillary bundle can be extended to the aroma chemical source by pushing the connecting tube from where the operator stands toward the direction of the aroma chemical source. The connecting tube slides along or within the support and the capillary tubes are thus extended outward. Once the aroma chemicals have been collected, the capillaries are pulled back into the support by pulling the connecting tube. Any manner of moving the connecting tube in the direction of the aroma source is deemed to be within the scope of the present invention.

It is preferable to protect the capillary bundle while it is being extended and maneuvered into position relative to the desired aroma-emitter. We have found that it is desirable to first insert the connecting tube holding the bundle into a housing sheath of semi-rigid material such as nylon which is substantially friction-free with respect to the connector. It is suitable, though, for the housing sheath to be tubular and it is connected or attached to the support or it can be connected or attached within a tubular support. A connecting tube of PTFE (TEFLON), for instance, must be freely moveable along the surface of the sheath. Accordingly, the connecting tube holding the capillaries can be extended beyond the end of the housing sheath when in proximity to a flower for collection.

Where the support is tubular and the sheath is attached therein, the support provides the actual barrier or protective covering to shield the capillary tubes from damage. Yet, the sheath which facilitates ready deployment of the capillaries after the apparatus has been extended into position through branches, etc., contributes to the protection of the capillaries.

It is also contemplated that the support can be prefabricated with an inner surface of sheath material.

In the preferred embodiment, the connecting tube within the housing sheath runs alongside the extendible pole. Fasteners can be used at one or more locations along the pole to fasten the sheath to the pole. The housing sheath can be run along the extendible pole beyond any hinge points, or preferably, into the support. This configuration advantageously permits free movement of the connecting tube by the operator pushing the tube at the proximal end of the housing sheath.

When a long pole is used with an attached support at the distal end, the housing sheath can be disposed on or in the support. Preferably, the housing sheath holds the connecting tube within, for the length of the pole. For a hollow extendible pole, the housing sheath runs along its exterior. As the housing sheath readily permits movement of the connecting tube, the connecting tube slides easily forward to extend the tubes for collection when the housing sheath is affixed alongside or throughout the entire length of the pole. It is suitable, though, to affix the housing sheath for about seventy-five percent of the length of the pole, where the sheath runs short at the proximal end of the pole.

The capillary bundle containing the trapped aroma chemicals is removed and carefully stored for subsequent processing. The aroma chemicals trapped within the capillaries of a bundle are then placed into a thermal desorber, for example, the Gertsel TDS 2. The desorbed volatiles are then transferred, using an inert gas such as helium at a flow rate of from 5–20 ml per minute, into a cryogenically cooled inlet that uses liquid nitrogen as coolant. The cryogenic focused materials are then analyzed directly by gas chromatography using an instrument such as a Hewlett Packard 6890 gas chromatograph equipped with a methyl silicone capillary column (0.125 mm×60 meter), and a mass spectrometer such as the Hewlett Packard 5973 mass spectral detector. Quantitative as well as qualitative analysis of the fragrance components can be performed. The analysis is simplified as the sample can be processed from the desorber through the mass spectrometer by the devices all connected in-line. We have surprisingly found that the process provides data of at least the same quality as the less practical existing methods.

As the present invention permits the capture of the headspace volatiles of a flower high up in the canopy, it will be apparent that when capture is performed in dense canopy, aroma molecules from adjacent aroma-emitters may also be captured. In this case, the captured molecules can represent some combination of aroma molecules from two or more aroma-emitting sources. Analysis of the adsorbed aroma chemicals from more than one source can identify desirable scent combinations.

BRIEF DESCRIPTION OF THE DRAWINGS

FIG. 2 illustrates the capture of aroma chemicals with a collection apparatus employing an extendible arm and a support attached thereto.

FIG. 2a illustrates the support of FIG. 2 in cross-section.

DETAILED DESCRIPTION OF THE DRAWINGS

Figure 1A:
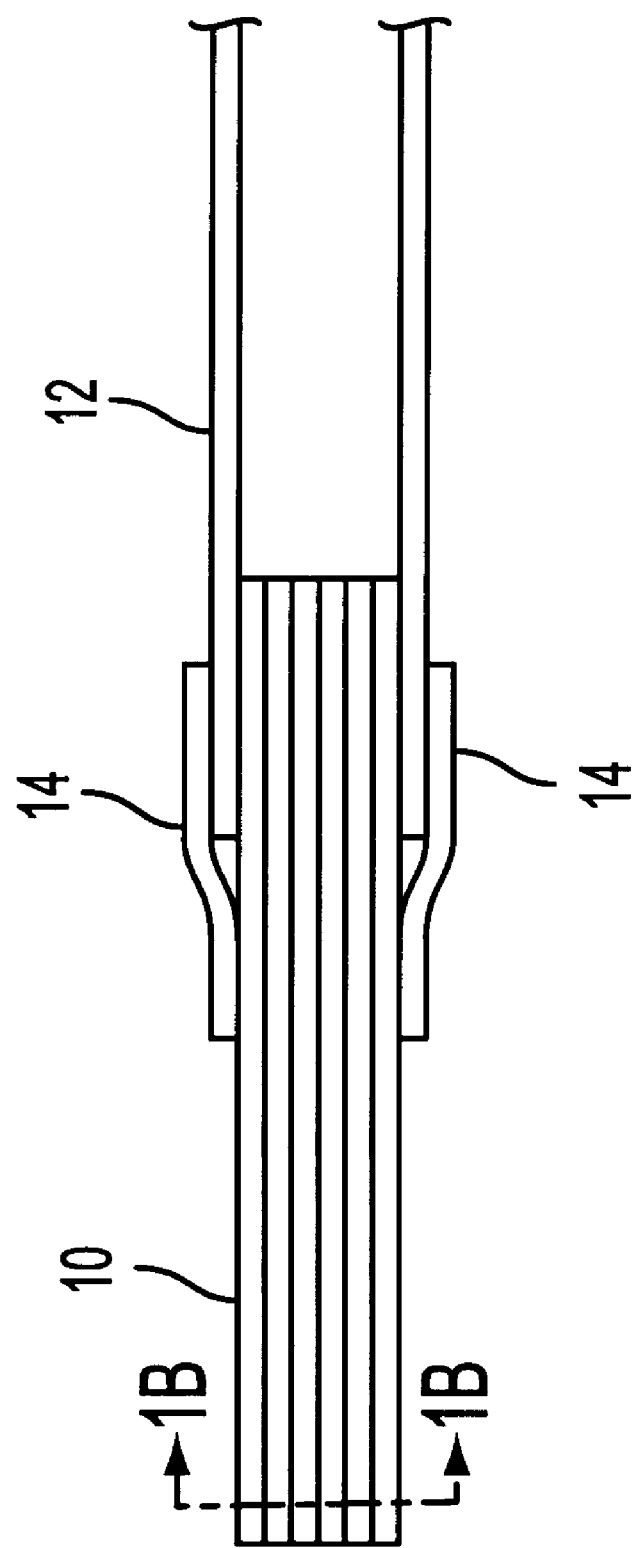
FIG. 1a illustrates a sectional view of a capillary tube bundle held within a connecting tube.
Figure 1B:
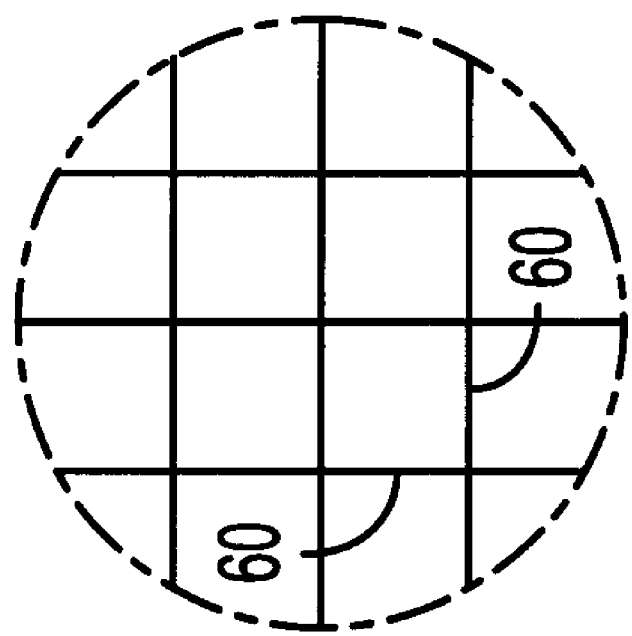
FIG. 1b illustrates a cross-sectional view of one of the capillary tubes having a plurality of crossing wall portions.

As illustrated in FIG. 1a, a bundle of capillary tubes 10 are held by connecting tube 12. The capillary tubes of bundle 10 are coated on their inner surfaces (not shown) with adsorbent materials of various polarities. Fastener 14 is fastened around connecting tube 12. FIG. 1b illustrates a cross-sectional view of one of the capillary tubes having a plurality of crossing wall portions 60.

Capillary bundle 10 is connected to a pump (not shown in FIG. 1) by connecting tube 12.

As illustrated in FIG. 2, aroma chemicals are obtained with a collection device employing support 26 which is attached by wing nut to extension arm 20. Extension arm 20 represents the distal portion of an extension device. Support 26 can swivel in this embodiment.

Capillary bundle 10 is shown over flower 18 collecting aroma chemicals. Connecting tube 12 is shown extended out from housing sheath 16. Housing sheath 16 runs within support 26 and emerges from aperture 28 of support 26 and runs alongside support 26 and extension arm 20. Fasteners 30 allow for loose fastening of housing sheath 16 to both support 26 and extension arm 20.

FIG. 2a illustrates a cross-section of support 26. Housing sheath 16 is within support 26, and connecting tube 12 is within housing sheath 16.

Figure 3:
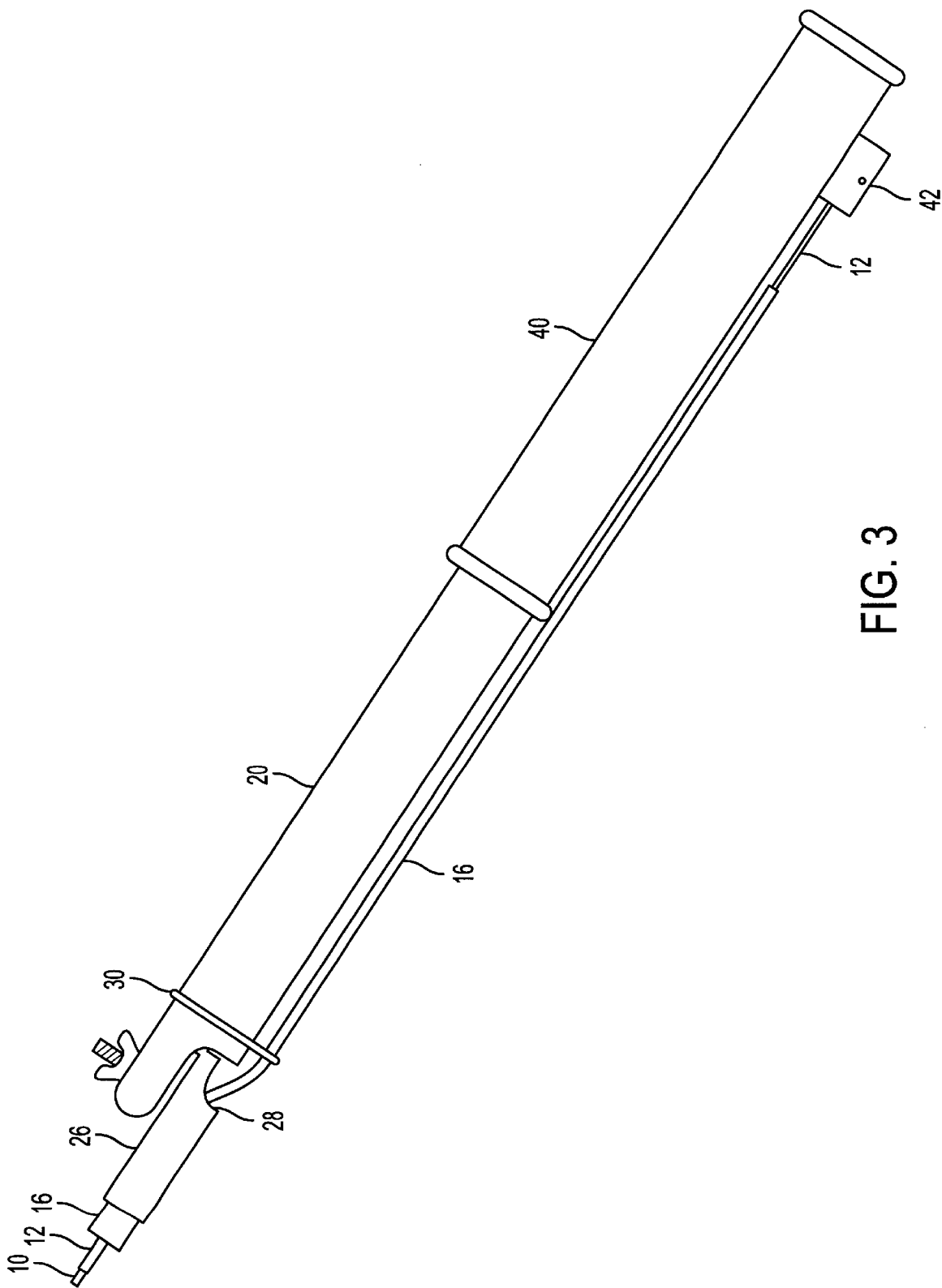
FIG. 3 illustrates apparatus for obtaining odors.

FIG. 3 illustrates a system for the collection of odors. A collection device is shown with extension device 40 having extension arm 20. Connecting tube 12 runs through housing sheath 16. Housing sheath 16 is within support 26 at its distal end and exits through aperture 28 of support 26 and continues along extension arm 20 and extension device 40. Connecting tube 12 emerges from housing sheath 16 and is operably connected to pump 42.

Figure 4:
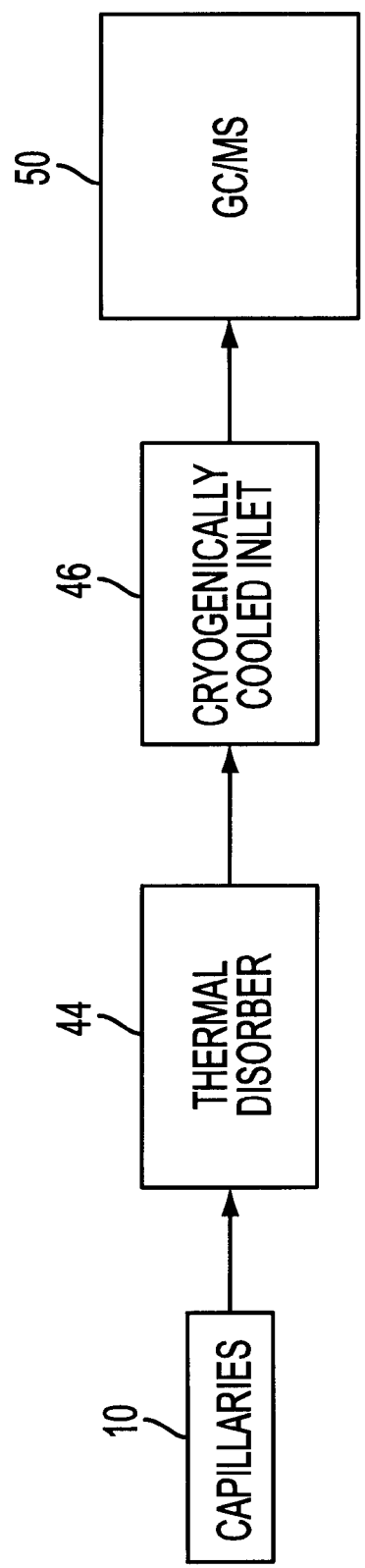
FIG. 4 illustrates apparatus for analyzing odors.

FIG. 4 illustrates the desorption and analysis of the captured aroma chemicals. After capture of aroma chemicals, the capillaries 10 are placed into thermal desorber 44. The desorbed volatiles are transferred into cryogenically cooled inlet 46. The cryogenically focused materials are then analyzed by GC/IMS instrument 50.

EXAMPLE 1

Scent was captured using three separate capillary bundles, each bundle having capillaries coated with Carbowax 20M® and capillaries coated with methyl silicone. By use of the aroma collection apparatus and method of the present invention, the aroma of a Hyacinth was collected. For the first capillary bundle, exposure of the coated capillaries to the headspace was for two minutes. For the second bundle, the collection time was five minutes and for the third, the bundle was exposed for ten minutes.

Each bundle of tubes was placed in the thermal desorber. The samples were thermally desorbed, cryogenically focused and then analyzed on a gas chromatograph. The gas chromatograph utilized a methyl silicone capillary column (0.125 mm×60 m), a helium gas flow rate of 1.5 ml/min, and was programmed from 40° C. to 250° C. at 4° per minute.

Figure 5:
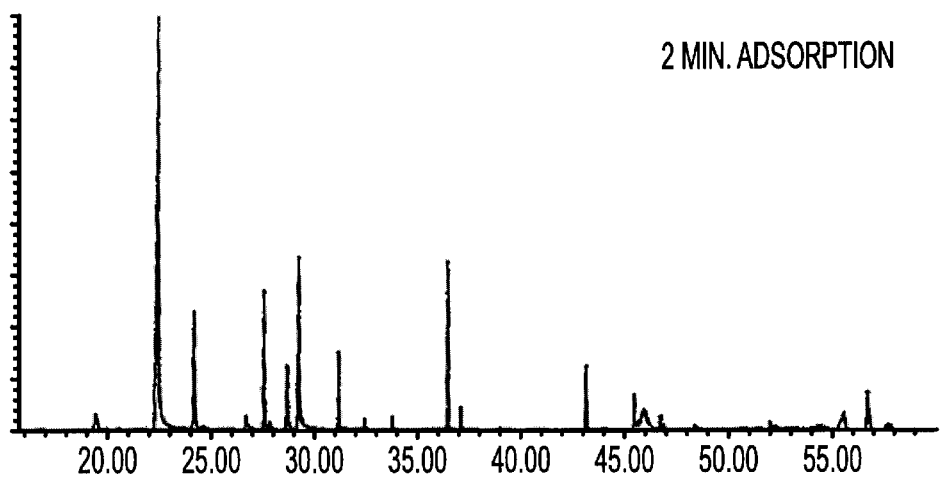
FIG. 5 illustrates a GC graph of resolved chemical components from a two minute aroma capture.

FIG. 5 is a graphical display of adsorption determined by GC for the first capillary bundle. The intensity of resolved odor chemicals is shown as a function of time. The amounts of the adsorbed components collected over a two minute period were sufficient to permit identification of the components by GC/MS.

Figure 6:
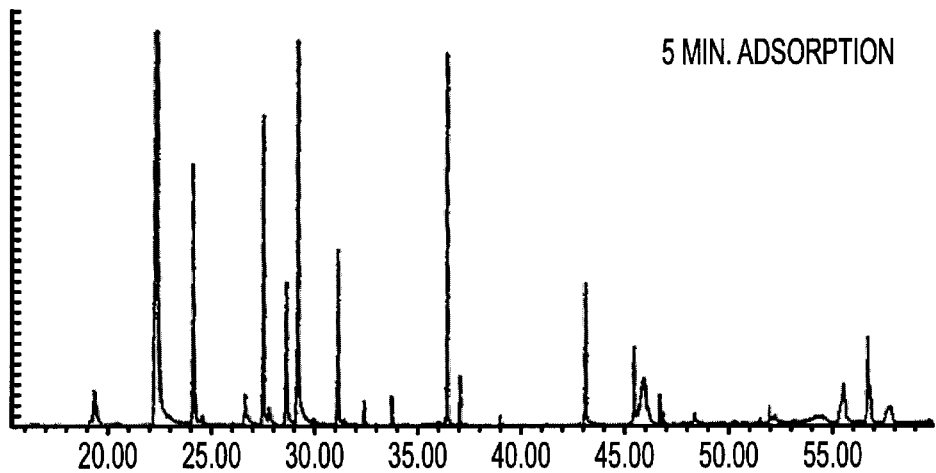
FIG. 6 illustrates a GC graph as in FIG. 5, where aroma capture was for five 5 minutes.

FIG. 6 is a graphical display as in FIG. 5 for the second capillary bundle. In comparing the relative intensities of corresponding peaks from FIG. 5, it can be seen that the intensity of the peaks is greater for a five minute adsorption time than for a two minute adsorption time. All peaks were easily identified by GC/MS.

Figure 7:
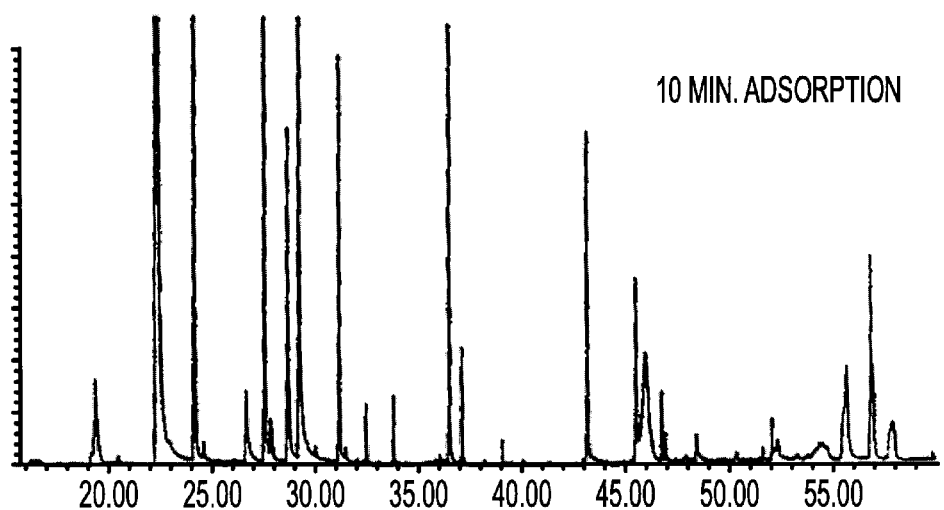
FIG. 7 illustrates a GC graph as in FIG. 5, where aroma capture was for ten 10 minutes.

FIG. 7 is also a graphical display as in FIG. 5 for the third capillary bundle. In comparing peak intensities, it can be seen that a greater amount of the aroma components can be adsorbed in ten minutes time then for two or five minutes.

As can be seen from FIGS. 5, 6, and 7, sufficient amounts of aroma chemicals can be collected, in a time period as low as two minutes, in sufficient quantities to permit analysis and identification of those chemicals.

While the invention has been illustrated and described with respect to illustrative embodiment and modes of practice, it will be apparent to those skilled in the art that various modifications and improvements may be made without departing from the scope and spirit of the invention. Accordingly, the invention is not to be limited by the illustrative embodiments and modes of practice.

What is claimed is:

1. An apparatus for obtaining odor chemicals comprising:
   an adsorbing unit comprising an interior surface of an adsorbent material;
   an extendible tubular pole for supporting the adsorbing unit;
   a suction device for drawing the odor chemicals into the unit; and
   a connecting tube which connects the unit and the suction device.

2. An apparatus according to claim 1 wherein the adsorbent material is selected from the group consisting of a polar adsorbent, a non-polar adsorbent, an intermediate polarity adsorbent, and any combination thereof.

3. An apparatus according to claim 2 wherein the polar adsorbent is Carbowax 20.

4. An apparatus according to claim 2 wherein the non-polar adsorbent is methyl silicone.

5. An apparatus according to claim 2 wherein the intermediate polarity adsorbent is selected from the group consisting of phenyl methyl silicone and polyacrylate.

6. An apparatus according to claim 1 wherein the adsorption unit is one or more capillary tubes.

7. An apparatus according to claim 6 wherein the adsorption unit is a plurality of capillary tubes.

8. An apparatus according to claim 7 wherein the plurality of capillary tubes consist of tubes coated with polar adsorbent, tubes coated with non-polar adsorbent, and tubes coated with intermediate polarity adsorbent.

9. An apparatus according to claim 7 wherein each tube has an internal diameter of from about 0.07 mm to about 1.0 mm.

10. An apparatus according to claim 9 wherein each tube has an internal diameter of from about 0.75 mm to about 0.9 mm.

11. An apparatus according to claim 7 wherein each tube is from about 5 mm to about 120 mm long.

12. An apparatus according to claim 7 wherein the plurality of capillary tubes are in a bundle that is less than 6 mm in diameter.

13. An apparatus according to claim 7 wherein each tube has a coating of adsorbent material which is from about 0.1 μm to about 1.25 μm thick.

14. An apparatus according to claim 1 wherein the suction device is a diaphragm pump.

15. An apparatus according to claim 1 where the connecting tube is made from PTFE.

16. An apparatus according to claim 1 wherein the support is made from a rigid material selected from the group consisting of glass, metal, wood, and stiff polymeric materials.

17. An apparatus according to claim 1 further comprising a housing sheath which is attached to the support and which holds the connecting tube and the adsorbing unit therein such that they are freely moveable.

18. An apparatus according to claim 17 wherein the housing sheath is a made from a semi-rigid material.

19. An apparatus according to claim 18 wherein the housing sheath is made from nylon.

20. An apparatus according to claim 17 further comprising means for extending the adsorbing unit beyond the end of the housing sheath for collection or odor chemicals.

21. An apparatus for capturing odor chemicals comprising:
- a plurality of capillary tubes which comprise interior surfaces comprising adsorbent material;
- a suction device for drawing the odor chemicals into the plurality of capillary tubes;
- a connecting tube which connects the plurality of capillary tubes and the suction device;
- a housing sheath within which the connecting tube and the plurality of capillary tubes are disposed such that the capillary tubes are freely moveable; and
- a support for the plurality of capillary tubes.

* * * * *